United States Patent [19]

Haugwitz

[11] 4,196,250

[45] Apr. 1, 1980

[54] POLYETHER DERIVATIVES

[75] Inventor: Rudiger D. Haugwitz, Titusville, N.J.

[73] Assignee: E. R. Squibb & Sons, Inc., Princeton, N.J.

[21] Appl. No.: 12,621

[22] Filed: Feb. 16, 1979

[51] Int. Cl.$^2$ .................. A61K 31/335; C07D 319/08
[52] U.S. Cl. .................................. 424/278; 260/340.3; 568/614
[58] Field of Search ....................... 260/340.3; 424/278

[56] References Cited

U.S. PATENT DOCUMENTS

| | | | |
|---|---|---|---|
| 4,051,189 | 9/1977 | Shepard et al. | 260/340.3 X |
| 4,086,244 | 4/1978 | Sprague | 260/340.3 |
| 4,104,275 | 8/1978 | Kauer | 260/340.3 X |

OTHER PUBLICATIONS

Current Abstracts of Chemistry, vol. 62, Issue 667, 1976 (247423).
Current Abstracts of Chemistry, vol. 66, Issue 717, 1977 (260233).
Vogtle, F. et al., *Angewandte Chem.*, 89(6), 410-412 (1977).
Popova, V. A. et al., *U.S.S.R. Khim-Farm* ZH 10(6), 66-68 (1976).
Christensen et al., *Chemical Reviews*, 1974, vol. 74, No. 3, pp. 351-384.
Gokel et al., *Synthesis*, Mar. 1976, pp. 168-178.

*Primary Examiner*—Ethel G. Love
*Attorney, Agent, or Firm*—Lawrence S. Levinson; Burton Rodney

[57] ABSTRACT

Polyether derivatives are provided having the formula

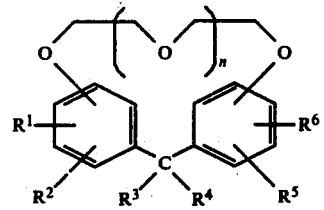

wherein $R^1$, $R^2$, $R^5$ and $R^6$ are the same or different and are hydrogen, halogen, nitro, lower alkyl or cyano; $R^3$ and $R^4$ are the same or different and are hydrogen, halogen or together represent =O; and n is 1 to 5. These compounds are useful as coccidiostats and antiinflammatory agents.

11 Claims, No Drawings

POLYETHER DERIVATIVES

DESCRIPTION OF THE INVENTION

The present invention relates to polyethers having the formula

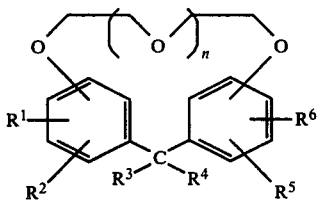

I wherein $R^1$, $R^2$, $R^5$ and $R^6$ may be the same or different and are hydrogen, halogen, nitro, lower alkyl or cyano; $R^3$ and $R^4$ may be the same or different and are hydrogen or halogen or $R^3$ and $R^4$ together represent oxygen (=O); and n is an integer of from 1 to 5. These compounds are useful as coccidiostats and anti-inflammatory agents.

In the above compounds, unless otherwise indicated, the term "lower alkyl" or "alkyl" as employed herein includes both straight and branched chain radicals of up to eight carbon atoms, preferably up to and including 5 carbon atoms, for instance, methyl, ethyl, n-propyl, isopropyl, n-butyl, t-butyl, isobutyl, n-pentyl, n-hexyl, isohexyl, n-heptyl, 4,4-dimethylpentyl, n-octyl, 2,2,4-trimethylpentyl, and the like.

The term "halogen" refers to Cl, Br or F, with Cl being preferred.

Preferred are those compounds of formula I wherein $R^1$ and $R^6$ are halogen, nitro or lower alkyl, and $R^2$, $R^3$, $R^4$ and $R^5$ are hydrogen or $R^2$ and $R^5$ are hydrogen and $R^3$ and $R^4$ together represent =O, n is 3 or 4, and the linking oxygens from the polyether are attached to the 2- or 4-position of each of the phenyl groups. More preferred are those compounds of formula I wherein $R^1$ and $R^6$ are halogen attached to the 5-position of each of the phenyl groups, $R^3$ and $R^4$ are each hydrogen, n is 3 and the linking oxygens of the polyether group are attached to the 2-position of each of the phenyl groups.

The compounds of formula I can be prepared from phenols II and a di-halogen derivative III in accordance with the following reaction

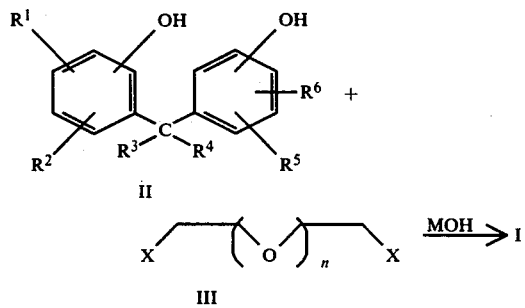

where X is Cl or Br
and M is Na or K

The reaction is preferably performed in a solvent such as n-butanol, propanol, diglyme at reflux temperatures for 1 to 24 hours in the presence of sodium or potassium hydroxide. The molar ratio of II to III to MOH is approximately 1:1:2. The requisite dihalogen derivative is prepared from the corresponding dihydroxy compound IV in accordance with the following reaction as described in J.A.C.S. 89, 7017 (1967).

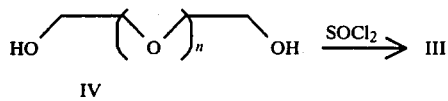

IV

The formula I compounds have coccidial activity, and thus may be used to treat any animal subject to coccidiosis infections, such as poultry, for example, chickens or turkeys. Thus, coccidial infections in chickens can be effectively controlled by the administration of an effective amount of compounds of formula I in the drinking water or feed of that chicken. An effective amount of formula I compound for controlling coccidiosis in chickens is at least the equivalent of 275 milligrams of active compound per kilogram of chicken body weight per week, administered for at least one week. When given in the drinking water of chickens the necessary concentration of formula I compound to insure administration of the above dosage is 0.025% by volume (250 parts per million) administered for one week.

The formula I compounds also have antiinflammatory activity as measured by the mouse active arthus (MAA) test and/or other related tests and are useful as antiinflammatory agents and may be used, for example, in a manner similar to phenylbutazone or indomethacin. They may be used to decrease joint swelling, tenderness, pain and stiffness in mammalian species, such as dogs, cats, monkeys, rats, mice and the like, e.g., in conditions such as rheumatoid arthritis. For this purpose these compounds may be incorporated in a conventional dosage form such as tablet, capsule, injectable or the like, along with the necessary carrier material, excipient, lubricant, buffer or the like, as will be seen hereinafter, for oral or parenteral administration in single or divided doses of about 1 to 150 mg/kg/day, preferably about 5 to 75 mg/kg, two to four times daily.

The compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following Examples represent preferred embodiments of the present invention.

EXAMPLE 1

2,20-Dichloro-6,7,9,10,12,13,15,16-octahydro-22H-dibenzo[n,q][1,4,7,10,13]pentaoxacyclo-octadecin

A. 1,11-Dichloro-3,6,9-trioxaundecane

A mixture of 430 g of tetraethylene glycol (2.2 moles), 2000 ml of dry benzene, and 386 g of pyridine (4.9 moles) is heated to reflux, and 580 g of thionyl chloride (4.9 moles) is added dropwise with stirring in three hours. During this period the reflux temperature of the mixture drops from 86° to 78°, and a white precipitate is formed. Heating is continued overnight (16 hours) and, after cooling, 50 ml of hydrochloric acid diluted with 200 ml of water is added dropwise in about 15 minutes. Benzene is removed from the upper layer containing the product, and the residue vacuum distilled at 4.5 mm Hg at 165°. The yield is 375 g of light yellow liquid (72%).

B. 2,20-Dichloro-6,7,9,10,12,13,15,16-octahydro-22H-dibenzo[n,q][1,4,7,10,13]-pentaoxacyclo-octadecin 10 g (0.037 mole) bis(2-hydroxy-5-chlorophenyl)-methane and 8.6 g (0.037 mole) 1,11-dichloro-3,6,9-trioxaundecane are dissolved in 100 ml n-BuOH. To this is added 6.5 g 50% aqueous sodium hydroxide. The resulting solution is heated to reflux for 15 hours, acidified with ethereal HCl, and solvent stripped in vacuo. The resulting gum is chromatographed on Neutral Alumina IV, eluting with ether/ethyl acetate. Appropriate fractions are collected, combined and recrystallized from methanol to yield 3.65 g white crystalline solid; m.p. 143.5°–144°. Yield: 23%.

EXAMPLE 2

2,4,18,20-Tetrachloro-6,7,9,10,12,13,15,16-octahydro-22H-dibenzo[n,q][1,4,7,10,13]pentaoxacyclo-octadecin Following the procedure of Example 1 but substituting bis-(2-hydroxy-3,5-dichlorophenyl)-methane for bis-(2-hydroxy-5-chlorophenyl)methane, 2,4,18,20-tetrachloro-6,7,9,10,12,13,15,16-octahydro-22H-dibenzo[n,q][1,4,7,10,13]pentaoxacyclo-octadecin is obtained.

EXAMPLE 3

2,23-Dibromo-6,7,9,10,12,13,15,16,18,19-decahydro-25H-dibenzo[q,t][1,4,7,10,13,16]hexaoxacycloundodecin Following the procedure of Example 1 but substituting bis-(2-hydroxy-5-bromophenyl)methane for bis-(2-hydroxy-5-chlorophenyl)methane and 1,14-dibromo-3,6,9,12-tetra-oxatetradecane for 1,11-dichloro-3,6,9-trioxaundecane, 2,23-dibromo-6,7,9,10,12,13,15,16,18,19-decahydro-25H-dibenzo-[q,t][1,4,7,10,13,16]hexaoxacycloundodecin is obtained.

EXAMPLES 4 to 13

Following the procedure of Example 1 except substituting for bis(2-hydroxy-5-chlorophenyl)methane the phenol shown in Column I of Table A below, and substituting for 1,11-dichloro-3,6,9-trioxaundecane the dihalogen polyether shown in Column II, the product shown in Column III is obtained.

TABLE A

| Ex. No. | Position of OH | $R^1$ | $R^2$ | $R^5$ | $R^6$ | $R^3$ | $R^4$ | n | X |
|---|---|---|---|---|---|---|---|---|---|
| 4. | 2 | H | H | Cl(4) | Cl(4) | H | H | 3 | Cl |
| 5. | 2 | H | H | Br(4) | Br(4) | H | H | 4 | Br |
| 6. | 2 | H | H | H | H | O | | 3 | Cl |
| 7. | 2 | Cl(2) | Cl(2) | Cl(5) | Cl(5) | H | H | 3 | Br |
| 8. | 2 | H | H | NO$_2$(5) | NO$_2$(5) | H | H | 4 | Cl |
| 9. | 4 | Cl(3) | Cl(3) | H | H | H | H | 4 | Br |

Column III

| Ex. No. | Position of Oxygen | $R^1$ | $R^2$ | $R^5$ | $R^6$ | $R^3$ | $R^4$ | n |
|---|---|---|---|---|---|---|---|---|
| 4. | 2 | H | H | Cl(4) | Cl(4) | H | H | 3 |
| 5. | 2 | H | H | Br(4) | Br(4) | H | H | 4 |

TABLE A-continued

| Ex. No. | Position of OH | R¹ | R² | R⁵ | R⁶ | R³ | R⁴ | n |
|---|---|---|---|---|---|---|---|---|
| 6. | 2 | H | H | H | H | =O | | 3 |
| 7. | 2 | Cl(2) | Cl(2) | Cl(5) | Cl(5) | H | H | 3 |
| 8. | 2 | H | H | NO₂(5) | NO₂(5) | H | H | 4 |
| 9. | 4 | Cl(3) | Cl(3) | H | H | H | H | 4 |

| | | Column I | | | | | | | Column II |
|---|---|---|---|---|---|---|---|---|---|
| Ex. No. | Position of OH | R¹ | R² | R⁵ | R⁶ | R³ | R⁴ | n | X |
| 10. | 4 | CH₃(2) | CH₃(2) | H | H | H | H | 3 | Cl |
| 11. | 2 | H | H | H | H | Cl | Cl | 3 | Cl |
| 12. | 2 | CN(5) | CN(5) | H | H | H | H | 5 | Br |
| 13. | 2 | Cl(3) | Cl(3) | Cl(5) | Cl(5) | H | H | 3 | Cl |

| | | Column III | | | | | | |
|---|---|---|---|---|---|---|---|---|
| Ex. No. | Position of Oxygen | R¹ | R² | R⁵ | R⁶ | R³ | R⁴ | n |
| 10. | 4 | CH₃(2) | CH₃(2) | H | H | H | H | 3 |
| 11. | 2 | H | H | H | H | Cl | Cl | 3 |
| 12. | 2 | CN(5) | CN(5) | H | H | H | H | 5 |
| 13. | 2 | Cl(3) | Cl(3) | Cl(5) | Cl(5) | H | H | 3 |

What is claimed is:

1. A compound of the structure

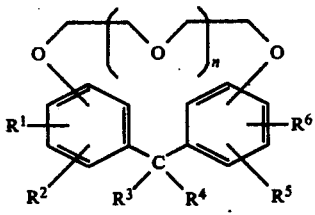

wherein $R^1$, $R^2$, $R^5$ and $R^6$ are the same or different and are hydrogen, halogen, nitro, lower alkyl or cyano, $R^3$ and $R^4$ are the same or different and are hydrogen or halogen or $R^3$ and $R^4$ together represent oxygen, and n is an integer from 1 to 5.

2. The compound of claim 1 wherein $R^2$ and $R^5$ are hydrogen, and $R^1$ and $R^6$ are halogen.

3. The compound of claim 1 wherein $R^3$ and $R^4$ are each hydrogen.

4. The compound of claim 1 wherein n is 3 or 4.

5. The compound of claim 1 wherein the linking oxygens of the polyether portion of the compound is linked to the 2- or 4-position of each phenyl ring.

6. The compound of claim 1 wherein $R^3$ and $R^4$ together represent =O.

7. The compound of claim 1 having the name 2,20-dichloro-6,7,9,10,12,13,15,16-octahydro-22H-dibenzo-[n,q][1,4,7,10,13]pentaoxacyclo-octadecin.

8. An anti-coccidial composition useful for treating coccidial infections in poultry comprising an anti-coccidial effective amount of a compound as defined in claim 1 and a pharmaceutically acceptable carrier therefor.

9. A method of treating coccidial infections in poultry, which comprises administering to poultry an anti-coccidial effective amount of a composition as defined in claim 8.

10. An anti-inflammatory composition comprising an anti-inflammatory effective amount of a compound as defined in claim 1 and a pharmaceutically acceptable carrier therefor.

11. A method for treating an inflammatory condition, which comprises administering to a mammalian host an anti-inflammatory effective amount of a compound as defined in claim 1.

* * * * *